(12) United States Patent
Goyal et al.

(10) Patent No.: US 10,625,020 B2
(45) Date of Patent: Apr. 21, 2020

(54) NEEDLE-FREE INJECTION GUIDE

(71) Applicant: Portal Instruments, Inc., Cambridge, MA (US)

(72) Inventors: Pragun Goyal, Cambridge, MA (US); Nikola Kojic, Winchester, MA (US)

(73) Assignee: Portal Instruments, Inc., Cambridge, MA (US)

( * ) Notice: Subject to any disclaimer, the term of this patent is extended or adjusted under 35 U.S.C. 154(b) by 1 day.

(21) Appl. No.: 15/357,036

(22) Filed: Nov. 21, 2016

(65) Prior Publication Data

US 2017/0143905 A1    May 25, 2017

Related U.S. Application Data

(60) Provisional application No. 62/258,654, filed on Nov. 23, 2015.

(51) Int. Cl.
*A61M 5/30* (2006.01)
*A61M 5/46* (2006.01)

(52) U.S. Cl.
CPC .......... *A61M 5/30* (2013.01); *A61M 5/3007* (2013.01); *A61M 5/46* (2013.01); *A61M 2209/04* (2013.01)

(58) Field of Classification Search
CPC ............ A61M 2005/1585; A61M 5/46; A61M 2005/1581; A61M 5/30; A61M 5/3007
See application file for complete search history.

(56) References Cited

U.S. PATENT DOCUMENTS

| | | | | |
|---|---|---|---|---|
| 2007/0232994 A1* | 10/2007 | Sonoda | ................... | A61M 5/46 604/68 |
| 2009/0227942 A1* | 9/2009 | Stroem Hansen | ...... | A61M 5/30 604/68 |
| 2015/0157787 A1 | 6/2015 | Cully et al. | | |

FOREIGN PATENT DOCUMENTS

| | | |
|---|---|---|
| WO | 2010/064211 A2 | 6/2010 |
| WO | 2011/011697 A1 | 1/2011 |

* cited by examiner

*Primary Examiner* — Deanna K Hall
(74) *Attorney, Agent, or Firm* — Occhiuti & Rohlicek LLP

(57) ABSTRACT

An injection guide globally aligns an injector to an angle selected for consistent subcutaneous delivery of an injectate, while locally aligning a patient's skin normal to the injection path at the location where the injection pierces the skin. This arrangement advantageously maintains controlled contact between an injector and a subject's skin in order to deliver the full, intended volume of injectate into the patient's subcutaneous layer while avoiding misdelivery into adjacent layers such as the patient's dermis or muscle.

20 Claims, 6 Drawing Sheets

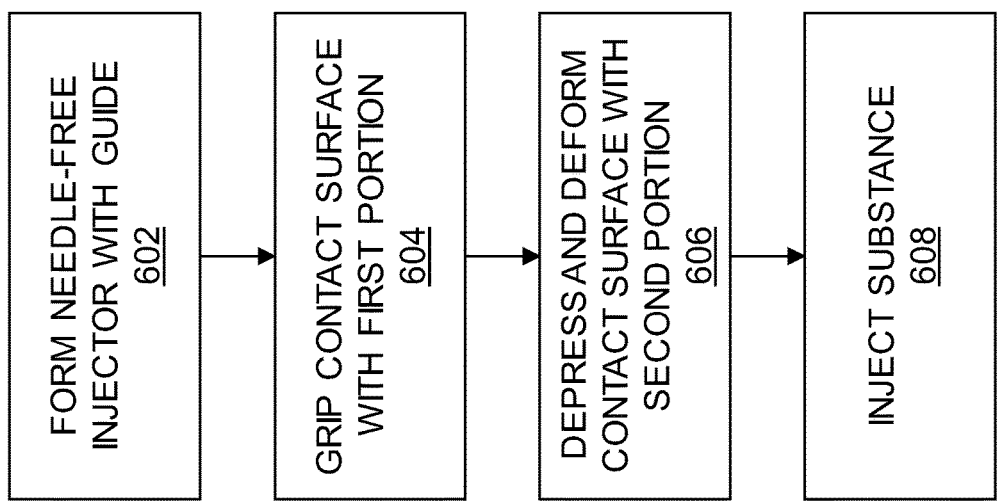

NEEDLE-FREE INJECTION GUIDE

CROSS REFERENCE TO RELATED APPLICATIONS

This application claims priority to U.S. Provisional Application No. 62/258,654, filed on Nov. 23, 2015, the contents of which are hereby incorporated by reference in their entirety.

BACKGROUND

An injected therapeutic typically has a designated injection route that is dependent on such factors as the timescale of the drug action, the dosage frequency, the required absorption rate for intended effect, and the target location(s). In particular, the subcutaneous (SC) space is considered to be useful for a number of applications and indications. When injecting into the SC space, ensuring that the injectate does not pass through the SC layer and into deeper layers is desirable because further penetration may reduce treatment efficacy, cause patient discomfort or pain, and damage internal tissue. There remains a need for needle-free injection guides that mitigate risks of over-penetration or under-penetration during needle-free injection into the subcutaneous space.

SUMMARY

An injection guide globally aligns an injector to an angle selected for consistent subcutaneous delivery of an injectate, while locally aligning a patient's skin normal to the injection path at the location where the injection pierces the skin. This arrangement advantageously maintains controlled contact between an injector and a subject's skin in order to deliver the full, intended volume of injectate into the patient's subcutaneous layer while avoiding misdelivery into adjacent layers such as the patient's dermis or muscle.

In a general aspect of the invention, an injection guide is used with a needle-free injector for administering an injectable substance to a target underlying a contact surface. The injection guide is configured to position the needle-free injector relative to the contact surface and includes a surface positioner configured to be disposed at a distal end of the needle-free injector. The surface positioner has an axis extending from a first end of the surface positioner to a second end of the surface positioner. The surface positioner includes an outer surface having a first section for gripping a first portion of the contact surface, the first section disposed at an acute angle relative to the axis and a second section having an opening configured to be spaced from a nozzle of the needle-free injector and for passing the injectable substance from the nozzle to the contact surface.

In another aspect, an injection guide disclosed herein includes an entrance to receive a stream of injectate from a needle-free injector, an exit for passage of the stream into a contact surface, and a passageway linearly coupling the entrance to the exit along an axis of travel for the stream of injectate through the injection guide. The injection guide may further include a first alignment surface providing a substantially planar region disposed at an acute angle to the axis, along with a second alignment surface positioned about the exit of the injection guide, the second alignment surface configured to locally orient the contact surface at a second angle to the axis different from the acute angle in a region about the exit.

Aspects may include one or more of the following features.

The second section of the surface positioner may be configured to depress and deform a second portion of the contact surface, such that the second portion is at a selected angle relative to the first portion of the contact surface. The selected angle may be between 5 degrees and 85 degrees, or the supplements thereof. The first section of the surface positioner may be in the form of an arcuate band. The section portion of the surface positioner may be in the form of a cylindrical tube having a taper. The arcuate band may be in the form of an ellipse having a major axis and a minor axis, the cylindrical tube positioned at a vertex along the major axis of the ellipse.

In another general aspect, a needle-free injector is configured for administering an injectable substance to a target underlying a contact surface. The needle-free injector has a distal end and includes a surface positioner disposed at the distal end of the needle-free injector. The surface positioner has an axis extending from a first end of the surface positioner to a second end of the surface positioner. The surface positioner includes an outer surface having a first section for gripping a first portion of the contact surface, the first section disposed at an acute angle relative to the axis, and a second section having an opening spaced from a nozzle of the needle-free injector for passing the injectable substance from the nozzle to the contact surface.

Aspects may include one or more of the following features.

The second section of the surface positioner may be configured to depress and deform a second portion of the contact surface such that the second portion of the contact surface is at a selected angle relative to the first portion of the contact surface. The selected angle may be between 5 degrees and 85 degrees, or the supplements thereof. The first section of the surface positioner may be in the form of an arcuate band. The second section of the surface positioner may be in the form of a cylindrical tube having a taper. The arcuate band may be in the form of an ellipse having a major axis and a minor axis, the cylindrical tube positioned at a vertex along the major axis of the ellipse.

In another general aspect, a method of using a needle-free injecting injector to administer an injectable substance to a target underlying a contact surface, the needle-free injector having a longitudinal axis includes positioning a first section of the needle-free injector at an acute angle relative to the longitudinal axis of the needle-free injector, gripping with the first section of the needle-free injector a first portion of the contact surface, and injecting the injectable substance to the contact surface through an opening at a second section of the needle-free injecting instrument, the opening spaced from a nozzle of the needle-free injector.

Aspects may include one or more of the following features.

The method may include using the second section of the needle-free injector to depress and deform a second portion of the contact surface such that the second portion of the contact surface is at a selected angle relative to the first portion of the contact surface. The selected angle may be between 5 degrees and 85 degrees, or the supplements thereof. The method may include forming the first section of the needle-free injector as an arcuate band. The method may include forming the second section of the needle-free injector as a cylindrical tube having a taper. The method may include forming the arcuate band in the form of an ellipse having a major axis and a minor axis, and positioning the cylindrical tube at a vertex along the major axis of the ellipse.

Aspects may have one or more of the following advantages.

Among other advantages, a needle-free injector having the above features increases the likelihood that the injectable substance is delivered into the subcutaneous layer and not into surrounding tissue layers, such as the dermis and muscle layers. The surface positioner includes an outer surface that grips the contact surface (i.e., skin) of the subject so that the injectable substance passing through the nozzle is injected through the epidermis and dermis and into the subcutaneous space. Gripping the contact surface stabilizes and maintains the position of the needle-free injector and prevents it from rocking from side to side. That is, in the event of relative movement (e.g., due to movement of the subject), the target remains fixed relative to the needle-free injector.

In certain embodiments, a section of the positioner also depresses and deforms a localized area of the contact surface such that the nozzle through which the injectable substance is injected at a substantially 90° angle relative to the contact surface. By injecting the substance at such an angle, the ability to maintain the substance within the subcutaneous layer is maximized and the risk of the injectable substance passing through to the adjacent tissue is minimized. In essence, by positioning the nozzle at an acute angle relative to the contact surface and then deforming a localized area of the contact surface such that the injection site is parallel to the nozzle (i.e., the injectable substance pierces the injection site at a 90° angle), the injectable substance is introduced along the subcutaneous layer rather than transverse to the layer. This approach for introducing the injectable surface is particularly advantageous because physical characteristics (i.e., thickness, hardness, elasticity, composition) vary from subject to subject. It is appreciated that although a 90° angle is preferable, there is still benefit to injecting the substance at angles offset from 90° (e.g., in a range between 5° and 85°, or the supplements thereof).

Other features and advantages of the invention are apparent from the following description, and from the claims.

DESCRIPTION OF DRAWINGS

FIG. 6 shows a method for guiding a needle-free injection.

DESCRIPTION

The embodiments will now be described more fully hereinafter with reference to the accompanying figures, in which preferred embodiments are shown. The foregoing may, however, be embodied in many different forms and should not be construed as limited to the illustrated embodiments set forth herein.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illustrate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," "front," "back," and the like, are words of convenience and are not to be construed as limiting terms.

Figure 1:
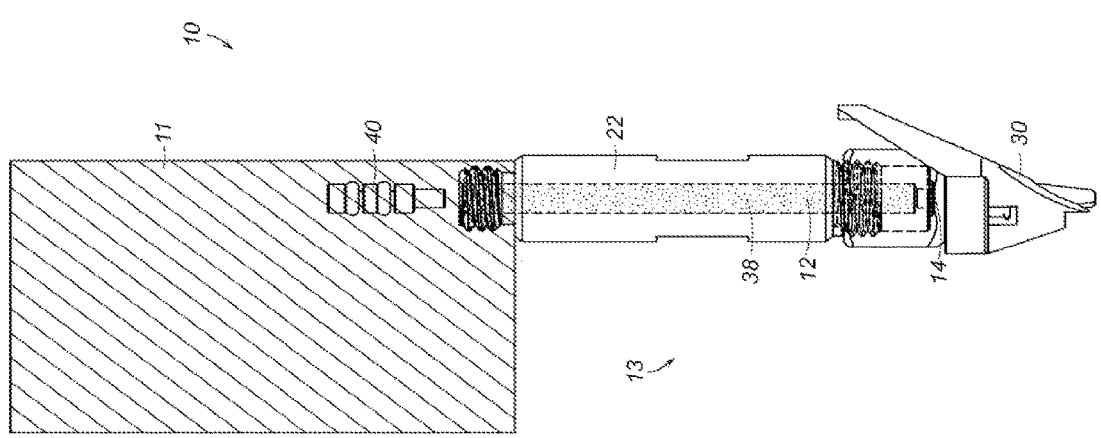
FIG. 1 is an embodiment of a needle-free injector having an injection guide.

Referring to FIG. 1, a needle-free injector 10 provides a patient with an injectate 12 (e.g., liquid medications, vaccines, and select solid dose implants) without the use of painful, sharp needles. The needle-free injector 10 may include an enclosure 11 with an injection head 13 attached thereto. The injection head 13 may include a primary container 22 having a bore 38 for receiving injectate. A plunger 40 may be sized and shaped for insertion into the bore 38 of the primary container 22 and a nozzle 14 may be disposed at a distal end of the primary container 22. The nozzle 14 may have an orifice (not shown) through which the injectate 12 is delivered to a patient. The enclosure 10 may include any suitable drive mechanism (not shown) for driving the plunger 40 into the bore 38 of the primary container 22 in a direction toward the distal end of the primary container 22 and forcing the injectate 12 out of the primary container 22 via the nozzle 14.

The needle-free injector 10 may be usefully employed with a variety of therapeutics including therapeutics that are repeatedly injected over regular intervals such as insulin, as well as high-viscosity or high-molecular-weight therapeutics such as monoclonal antibodies that might otherwise present physical difficulties for controlled injection. More generally, any therapeutic, medicine, or the like, may be usefully injected using a needle-free injector 10 as described herein.

In order to control an angle of injection, or more generally to provide for more consistent positioning of the needle-free injector during an injection procedure, the needle-free injector 10 may include an injection guide 30 that is positioned at the distal end of the drive head 13 of the needle-free injector 10 and over the nozzle 14. In general, the injection guide 30 may be removably and replaceably attached to the needle-free injector 10, e.g., using a snap fit, friction fit, screw fit, or other type of mechanical engagement. In another aspect, the injection guide 30 may be permanently affixed to or integrated into a body of the needle-free injector 10 or the primary container 22.

Figure 2:
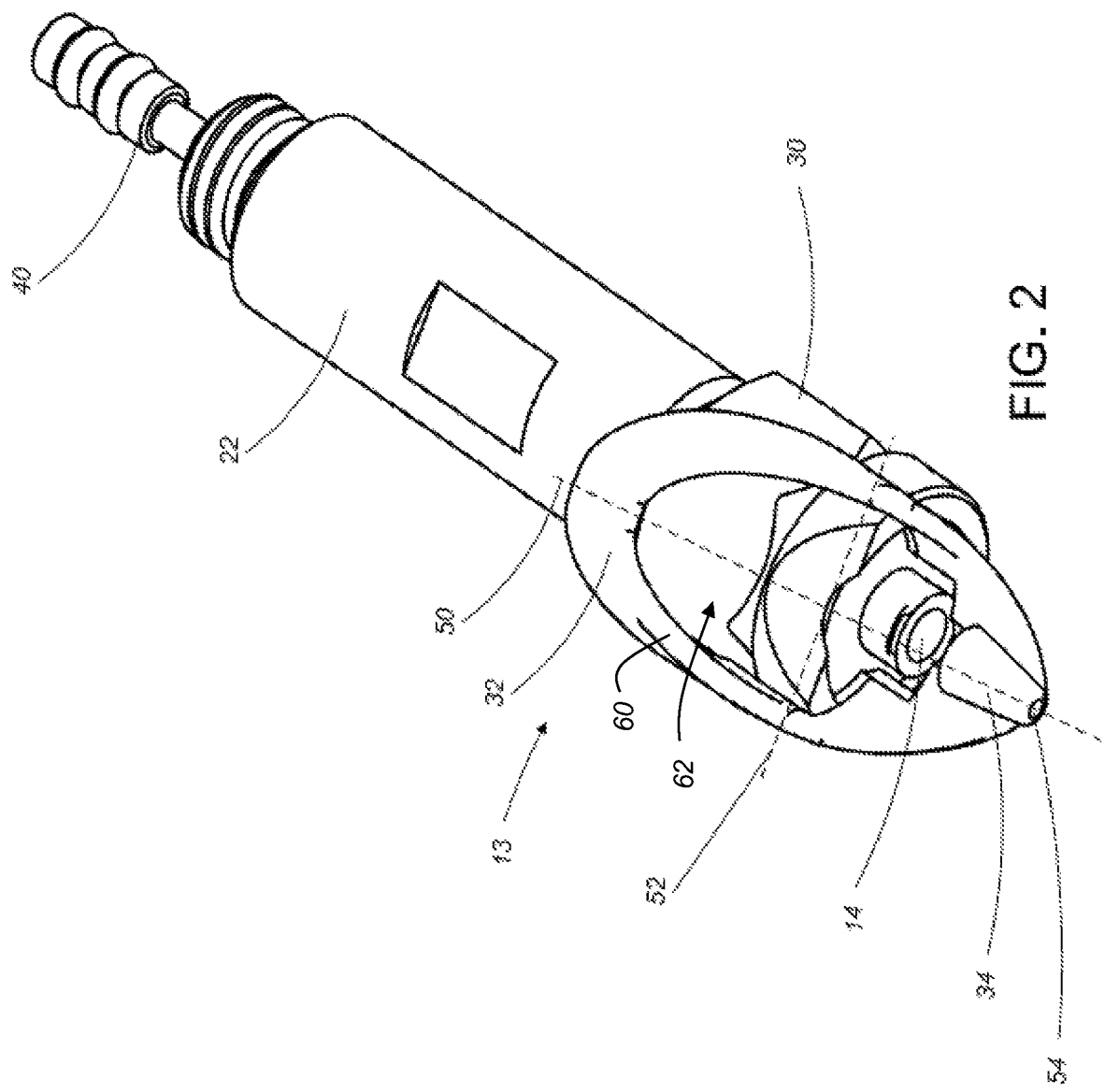
FIG. 2 is an injection head including the injection guide of FIG. 1.

Referring to FIG. 2, the injection guide 30 may include an outer surface having a first section 32 for gripping a first portion of a contact surface (e.g., a patient's skin) and a second section 34 which serves as a depressor. In this embodiment, the first section 32 of the injection guide 30 is elliptical in shape with a major axis 50 extending along the length of the needle-free injector and a minor axis 52 extending transverse to the major axis 50, however any size or shape of surface suitable for resting in contact with an injection site may also or instead be used. For example, the first section 32 may provide a relatively large and substantially planar surface to rest on the skin of a subject and align an injection as desired. While the first section 32 may usefully present a generally planar surface for generic stabilization, the first section 32 may also or instead be shaped to conform to a physiological region of interest such as the lateral upper arm or thigh (e.g., for subcutaneous injections).

In one aspect, the first section 32 of the injection guide 30 may be formed as an arcuate band. The first section 32 may also or instead be shaped to mitigate slipping or other non-normal movement of the needle-free injector 10, e.g., by providing protrusions, openings, or other surface variations to reduce or prevent movement parallel to the contact surface when placed for use in an injection. For example, the first section 32 may form an alignment surface that includes a perimeter 60 defining a substantially planar region (as shown, for example, in FIG. 5 below) and an open region 62 within the perimeter 60. The substantially planar region may provide global orientation of the injector to a desired injection path, and the open region 62 may provide lateral stability by receiving, deforming and gripping a portion of the contact surface to prevent sliding when placed for use. More generally, any shape that provides a projection normal to the contact surface 30 suitable for stabilizing a needle-free injector 15, and that provides features for mitigating lateral movement, may be usefully employed in the first section 32 of the injection guide 30 as contemplated herein.

The second portion 34 of the injection guide 30 may be formed as a tapered cylindrical tube. The second section 34 may include a through-hole 54 or passageway through which an injection jet originating from the nozzle 14 is able to travel. The second section 34 may be offset from the nozzle 14 by an offset distance so that the second section 34 protrudes past a plane formed by the first section 32 and into the contact surface. In this manner, the second section 34 may apply additional force to the surface of the skin (or other contact surface) so the second section 34 is able to locally reorient the contact surface at the injection site.

Thus the injection guide 30 may globally orient an injection axis to an injection site using the first section 32, and the injection guide 30 may locally orient the injection axis to a target surface of the injection site using the second section 34. Further, by separating the exit of the injection guide 30 from an entrance where the stream of injectate begins, the injection guide 30 may allow for degassing of the injectate during injection.

Figure 3:
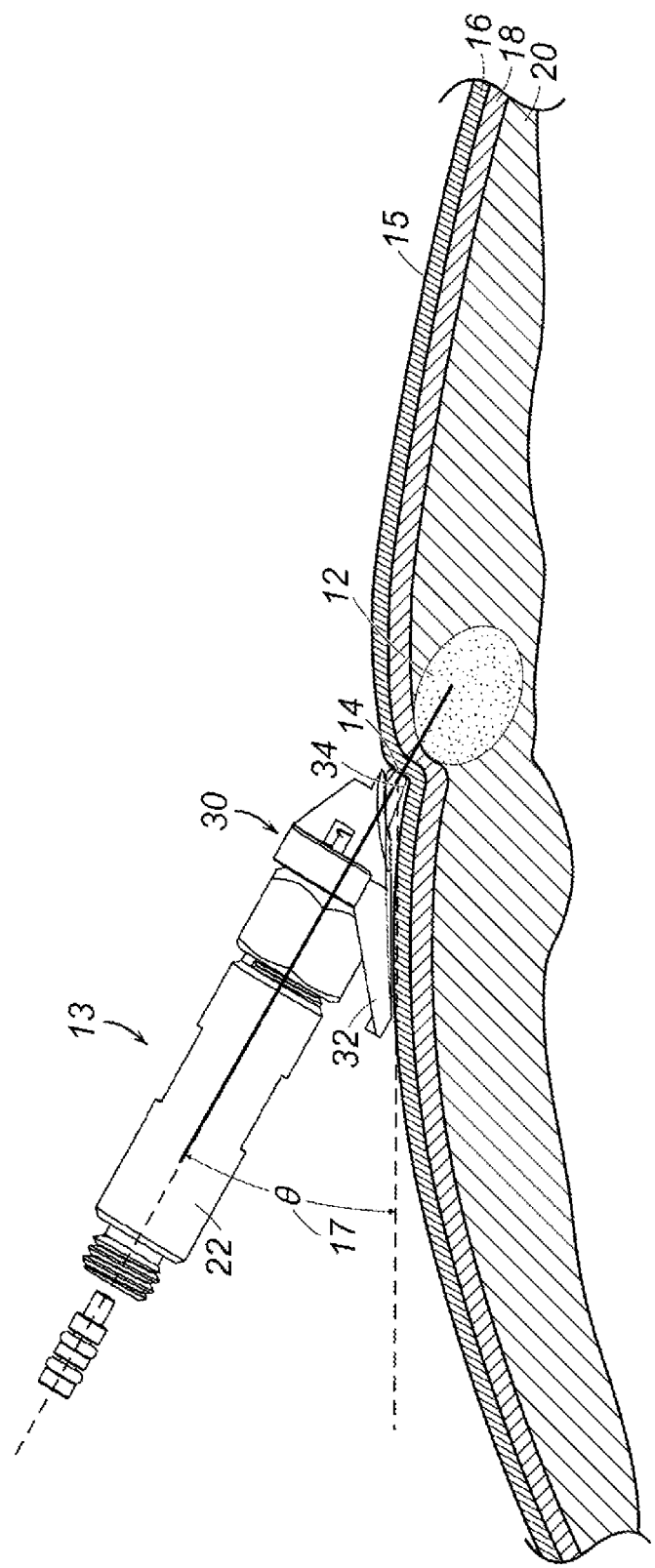
FIG. 3 shows the needle-free injector of FIG. 1 in operation.

Referring to FIG. 3, when place for use in contact with a patient's skin, the injection guide 30 may serve as a positioner for positioning a needle-free injector 10 relative to the patient's skin (i.e., contact surface 15 of the patient). Specifically, the injection guide 30 may retain the needle free injector 10 at an acute angle 17 (shown as angle, θ), in FIG. 3) relative to the contact surface 15. The acute angle 17 is preferred to be in a range between 10° and 80°, more preferably between 30° and 70°, and still more preferably between 40° and 60°. In one aspect, the acute angle may be less than 45°.

Once the first section 32 of the injection guide 30 is placed for use in contact with the contact surface 15, a slight normal force can stabilize the injection guide 30 (and the connected injector) laterally by causing the injection guide 30 to grip the contact surface 15 and limit lateral movement or sliding along the contact surface 15. Thus the first section 32 may be shaped and sized to concurrently stabilize the injection angle (based on alignment of the substantially planar surface and the contact surface 15) and the position (by preventing lateral slippage). At the same time, the second section 34 of injection guide 30 may extend beyond the planar surface and into the contact surface 15 such that when the injection guide 30 is placed for use and the needle-free injector 10 is actuated, the contact surface 15 is maintained locally normal to an axis of injection and the injectate 12 is delivered through an epidermis layer 16 at an angle approximating 90° (or at some other controlled angle, as appropriate).

Figure 4:
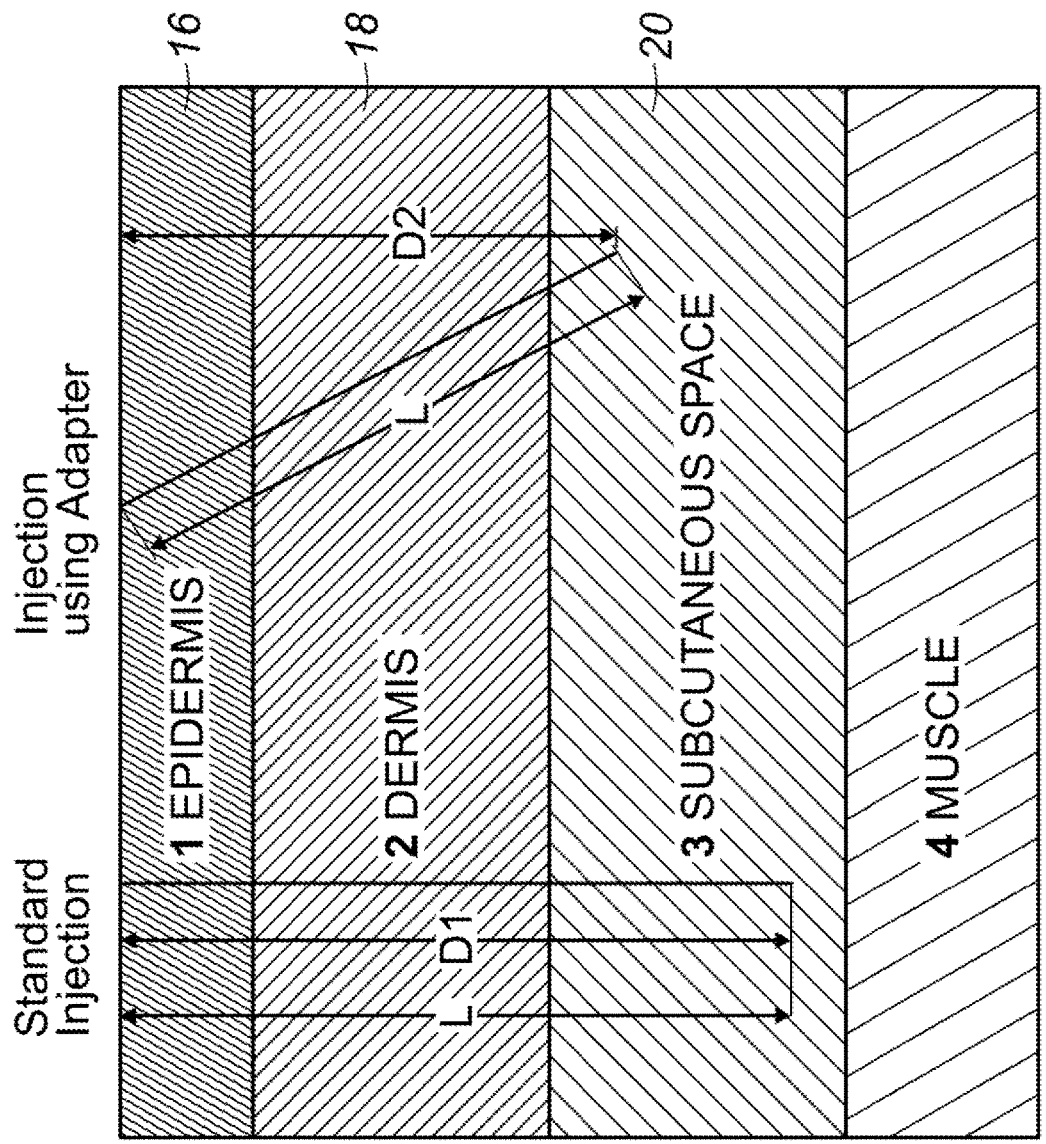
FIG. 4 is a comparison of a standard needle-free injection to a needle-free injection using the injection guide of FIG. 1.

Referring to FIG. 4, a comparison between a standard injection into a patient's skin and an injection into the patient's skin using the injection guide 30 shows that both injections have similar injection lengths, L but different injection depths, D1, D2, through the epidermis 16, the dermis 18, and into the subcutaneous space 20. The injection using the injection guide 30 results in an injection depth, D2 that is shallower than an injection depth, D1 of the standard injection due to its acute injection angle. By providing a longer path through the subcutaneous space 20, this angled trajectory can advantageously provide a greater margin for error by increasing the length of the path within the relevant tissue region (e.g., the subcutaneous space 20).

The injection guide 30 may be removably and replaceably attached to the needle-free injector 10 using any suitable means. For example, the injection guide 30 may be threaded onto the needle-free injector 10, or the injection guide 30 may snap onto the needle-free injector or engage the needle-free injector with a friction fit between suitably shaped and sized mating surface. The injection guide 30 may instead be integrated into the needle-free injector 10 as a single, molded part, or permanently attached to the needle-free injector 10 using an adhesive, ultrasonic welding, or any other assembly or attachment technique. The injection guide 30, and the various surfaces thereof, may be designed to accommodate a particular injection site, or a number of different injection sites which may be selected from any of a number of conventional injection sites including but not limited an arm, a thigh, an abdomen, a buttocks, and or any other appendage or other suitable injection site. The preferred site(s) may depend, for example, on the type of medicine, type of injection (e.g., the tissue layer for delivery of an injectate), frequency of injections, patient preferences, and so forth.

Figure 5:
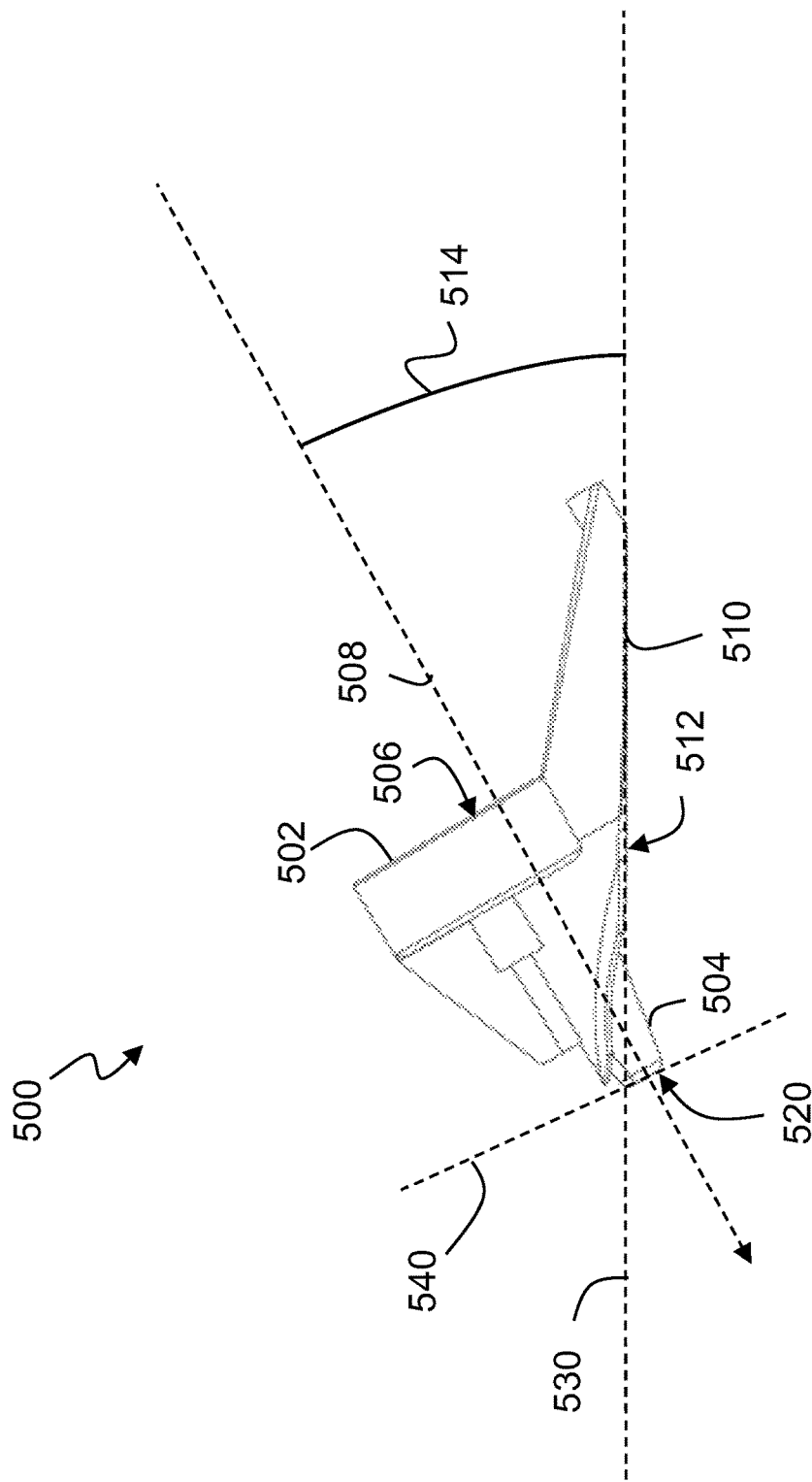
FIG. 5 shows a cross-section of an injection guide.

FIG. 5 shows a cross-section of an injection guide. The injection guide 500 may include any of the injection guides described herein. In general, the injection guide 500 may include an entrance 502 to receive a stream of injectate (not shown) from a needle-free injector 15, an exit 504 for passage of the stream into a contact surface, and a passageway 506 linearly coupling the entrance 502 to the exit 504 along an axis 508 of travel for the stream of injectate through the injection guide 500. In one aspect, the injection guide 500 may be a removable injection guide 500 and the entrance 502 may be shaped and sized to be removably and replaceably coupled to a needle-free injector 15 through any suitable mechanical or other means.

The injection guide 500 may include a first alignment surface 510 in order to globally align the needle-free injector 15 to a desired injection path, more specifically by aligning the axis 508 relative to the contact surface as desired when the injection guide 500 is placed for use on the contact surface. To this end, the first alignment surface 510 may provide a substantially planar region 512 lying within a first plane 530 disposed at an acute angle 514 to the axis 508. Thus the substantially planar region 512 of the first alignment surface 510 may be shaped and sized to retain the axis 508 of the passageway 506 at the acute angle 514 relative to the contact surface when the first alignment surface 510 is place for use against the contact surface.

The injection guide 500 may also include a second alignment surface 520 positioned about the exit 504 of the injection guide 500. The second alignment surface 520 may be configured to locally orient the contact surface at a second angle to the axis different from the acute angle in a region about the exit. For example, the second alignment surface 520 may wholly or partially lie in a second plane 540 substantially normal to the axis 508 of travel for the stream of injectate. When the injection guide 500 is placed for use on a pliable contact surface, the contact surface may conform to this second alignment surface 520 so that the contact surface is correspondingly maintained normal to the axis 508 around the exit 504.

The second alignment surface 520 may also or instead extend through or beyond the substantially planar region 512 of the first alignment surface 510 in a direction of travel of an injectate—that is, crossing through the first plane 530 associated with the substantially planar surface 512 of the first alignment surface 510—so that the exit 504 protrudes through the first plane 530 and into a contact surface. In this configuration, the second alignment surface 520 can more readily deform the contact surface into an orientation normal to the axis 508 for the injectate. More generally, the second alignment surface 520 may retain the contact surface locally about the exit 504 at any suitable angle for injection relative to the axis 508, such as normal to the axis 508 or at some other useful angle different from the acute angle between the axis 508 and the contact surface.

As described above, the injection guide 500 may also include a needle-free injector, which may be permanently attached or removably and replaceably attached thereto. The needle-free injector may contain any suitable injectate such as any of the therapeutics described herein, or any other useful therapeutic, medication, or other substance that might be usefully injected into a subject.

FIG. 6 shows a method for using a needle-free injector to administer an injectable substance to a target underlying a contact surface guiding a needle-free injection. In general, the method 600 may include any suitable method for forming and using any of the needle-free injection guides described herein.

As shown in step 602, the method may begin with forming a needle-free injector with an injection guide such as any of the guides described above. This may include forming a separate injection guide and coupling it to the needle-free injector, or this may include forming the injection guide integrally into the needle-free injector. In general, forming the needle-free injector may include forming a first section of the needle-free injector as an arcuate band or other shape configured to support the needle-free injector in a predetermined angular orientation with a contact surface when placed for use on the contact surface. The arcuate band may, for example, be in the form of an ellipse having a major axis and a minor axis. Forming the needle-free injector may further include forming a second section of the needle-free injector as a cylindrical tube having a taper, which cylindrical tube may be positioned at a vertex along the major axis of the ellipse. More generally, any suitable geometrical arrangement consistent with global and/or local alignment of an injection as contemplated herein may also or instead be used.

In one aspect, the needle-free injector may have a longitudinal axis parallel to a path of an injection stream, and forming the injection guide may further include positioning the first section of the needle-free injector at an acute angle relative to the longitudinal axis of the needle-free injector.

As shown in step 604, the method 600 may include gripping a first portion of a contact surface such as a patient's skin with the first section of the needle-free injector such that the longitudinal axis is maintained at the acute angle relative to the contact surface.

As shown in step 606, the method 600 may include using the second section of the needle-free injector to depress and deform a second portion of the contact surface such that the second portion of the contact surface is at a selected angle relative to the first portion of the contact surface. In this manner, the contact surface can be deformed into an orientation that is locally normal to the injection axis, or at some other predetermined angle to the injection axis (e.g., the longitudinal axis of the injector) different than the acute angle of the first portion of the needle-free injector. The selected angle may, for example, be between five degrees and eighty-five degrees, or supplements thereof, or the selected angle may be any other angle suitable for use in a needle-free injection.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. An injection guide for use with a needle-free injector for administering an injectable substance to a target underlying a contact surface, the injection guide configured to position the needle-free injector relative to the contact surface, the injection guide comprising:
   a surface positioner configured to be disposed at a distal end of the needle-free injector and having an axis extending from a first end of the surface positioner to a second end of the surface positioner, the surface positioner including an outer surface having:
   a first section for gripping a first portion of the contact surface, the first section disposed at an acute angle relative to the axis, and
   a second section having an opening configured to be spaced from a nozzle of the needle-free injector during administration of the injectable substance to allow for degassing of the injectable substance while passing the injectable substance from the nozzle to the contact surface when placed for use on the contact surface.

2. The injection guide of claim 1, wherein the second section of the surface positioner is configured to depress and deform a second portion of the contact surface, such that the second portion is at a selected angle relative to the first portion of the contact surface.

3. The injection guide of claim 2, wherein the selected angle is between five degrees and eighty-five degrees.

4. The injection guide of claim 3, wherein the first section of the surface positioner forms an arcuate band.

5. The injection guide of claim 4, wherein the second section of the surface positioner forms a cylindrical tube having a taper.

6. The injection guide of claim 5, wherein the arcuate band forms an ellipse having a major axis and a minor axis, the cylindrical tube positioned at a vertex along the major axis of the ellipse.

7. A needle-free injector for administering an injectable substance to a target underlying a contact surface, the needle-free injector having a distal end and comprising:
   a surface positioner disposed at the distal end of the needle-free injector and having an axis extending from a first end of the surface positioner to a second end of the surface positioner, the surface positioner including an outer surface having:
      a first section for gripping a first portion of the contact surface, the first section disposed at an acute angle relative to the axis, and
      a second section having an opening spaced from a nozzle of the needle-free injector during administration of the injectable substance to allow for degassing of the injectable substance while passing the injectable substance from the nozzle to the contact surface when placed for use on the contact surface.

8. The needle-free injector of claim 7, wherein the second section of the surface positioner is configured to depress and deform a second portion of the contact surface such that the second portion of the contact surface is at a selected angle relative to the first portion of the contact surface.

9. The needle-free injector of claim 8, wherein the selected angle is between five degrees and eighty-five degrees.

10. The needle-free injector of claim 9, wherein the first section of the surface positioner is in the form of an arcuate band.

11. The needle-free injector of claim 10, wherein the second section of the surface positioner forms a cylindrical tube having a taper.

12. The needle-free injector of claim 11, wherein the arcuate band forms an ellipse having a major axis and a minor axis, the cylindrical tube positioned at a vertex along the major axis of the ellipse.

13. An injection guide comprising:
   an entrance to receive a stream of injectate from a needle-free injector;
   an exit for passage of the stream into a contact surface;
   a passageway linearly coupling the entrance to the exit along an axis of travel for the stream of injectate through the injection guide, the passageway separating the entrance from the exit when placed for use on the contact surface and during injection of the injectate to allow degassing of the injectate during injection;
   a first alignment surface providing a substantially planar region disposed at an acute angle to the axis; and
   a second alignment surface positioned about the exit of the injection guide, the second alignment surface configured to locally orient the contact surface at a second angle to the axis different from the acute angle in a region about the exit.

14. The injection guide of claim 13 wherein the second alignment surface is substantially normal to the axis of travel for the stream of injectate.

15. The injection guide of claim 13 wherein the second alignment surface extends beyond the substantially planar region of the first alignment surface in a direction of travel of the injectate in order to retain the contact surface locally about the exit at the second angle to the axis.

16. The injection guide of claim 13 wherein the first alignment surface includes a perimeter defining the substantially planar region and an open region within the perimeter.

17. The injection guide of claim 13 further comprising the needle-free injector, wherein the needle-free injector is coupled to the entrance of the needle-free injector and wherein the needle-free injector contains the injectate.

18. The injection guide of claim 17 wherein the injectate includes a high-molecular weight therapeutic.

19. The injection guide of claim 17 wherein the injectate includes a high-viscosity therapeutic.

20. The injection guide of claim 13 wherein the acute angle is less than forty-five degrees.

* * * * *